(12) United States Patent
Richardson et al.

(10) Patent No.: US 7,032,459 B2
(45) Date of Patent: *Apr. 25, 2006

(54) STRUCTURES INCLUDING NETWORK AND TOPOLOGY FOR IDENTIFYING, LOCATING AND QUANTIFYING PHYSICAL PHENOMENA

(75) Inventors: John G. Richardson, Idaho Falls, ID (US); Karen A. Moore, Idaho Falls, ID (US); Robert A. Carrington, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 7 days.

This patent is subject to a terminal disclaimer.

(21) Appl. No.: 10/992,440

(22) Filed: Nov. 17, 2004

(65) Prior Publication Data

US 2005/0097965 A1    May 12, 2005

Related U.S. Application Data

(62) Division of application No. 10/074,598, filed on Feb. 11, 2002, now Pat. No. 6,889,557.

(51) Int. Cl.
*G01N 3/32* (2006.01)

(52) U.S. Cl. ....................................................... 73/809

(58) Field of Classification Search ................ 73/772, 73/774, 775, 763, 767, 809
See application file for complete search history.

(56) References Cited

U.S. PATENT DOCUMENTS

| | | | |
|---|---|---|---|
| 2,488,195 A | 11/1949 | Ivey | |
| 3,740,522 A | 6/1973 | Muehlberger | |
| 3,742,350 A | 6/1973 | White | |
| 4,092,950 A | 6/1978 | Hart | |
| 4,340,010 A | 7/1982 | Hart | |
| 4,420,251 A | 12/1983 | James et al. | |
| 4,472,621 A | 9/1984 | Blackmore | |
| 4,514,443 A | 4/1985 | Kostecki | |
| 4,529,974 A | 7/1985 | Tanaka et al. | |
| 4,661,682 A | 4/1987 | Gruner et al. | |
| 4,677,371 A | 6/1987 | Imaizumi | |
| 4,704,985 A | 11/1987 | Rubinstein | |
| 4,736,157 A | 4/1988 | Betker et al. | |
| 4,774,905 A | 10/1988 | Nobis | |
| 4,853,515 A | 8/1989 | Willen et al. | |
| 4,926,165 A | 5/1990 | Lahlouh et al. | |
| 5,015,958 A | 5/1991 | Masin et al. | |

(Continued)

FOREIGN PATENT DOCUMENTS

DE        3740498        6/1989

(Continued)

*Primary Examiner*—Max Noori
(74) *Attorney, Agent, or Firm*—Trask Britt, PC

(57) ABSTRACT

A method and system for detecting, locating and quantifying a physical phenomena such as strain or a deformation in a structure. A plurality of laterally adjacent conductors may each include a plurality of segments. Each segment is constructed to exhibit a unit value representative of a defined energy transmission characteristic. A plurality of identity groups are defined with each identity group comprising a plurality of segments including at least one segment from each of the plurality of conductors. The segments contained within an identity group are configured and arranged such that each of their associated unit values may be represented by a concatenated digit string which is a unique number relative to the other identity groups. Additionally, the unit values of the segments within an identity group maintain unique ratios with respect to the other unit values in the identity group.

20 Claims, 6 Drawing Sheets

U.S. PATENT DOCUMENTS

| | | |
|---|---|---|
| 5,024,423 A | 6/1991 | Matsumoto et al. |
| 5,181,962 A | 1/1993 | Hart |
| 5,185,183 A | 2/1993 | Gonda et al. |
| 5,254,820 A * | 10/1993 | Pesheck et al. ............. 219/752 |
| 5,279,148 A | 1/1994 | Brandes |
| 5,369,366 A | 11/1994 | Piesinger |
| 5,410,255 A | 4/1995 | Bailey |
| 5,412,173 A | 5/1995 | Muehlberger |
| 5,551,484 A | 9/1996 | Charboneau |
| 5,573,814 A | 11/1996 | Donovan |
| 5,743,299 A | 4/1998 | Chick et al. |
| 5,951,761 A | 9/1999 | Edstrom |
| 6,058,978 A | 5/2000 | Paletta et al. |
| 6,085,413 A | 7/2000 | Klassen et al. |
| 6,194,890 B1 | 2/2001 | Doyle et al. |
| 6,197,168 B1 | 3/2001 | Matsunaga et al. |
| 6,320,400 B1 | 11/2001 | Black et al. |
| 6,626,244 B1 * | 9/2003 | Powers ....................... 166/373 |
| 2001/0027708 A1 * | 10/2001 | Stewart et al. ................. 83/177 |
| 2003/0047317 A1 * | 3/2003 | Powers ....................... 166/373 |
| 2003/0161946 A1 | 8/2003 | Moore et al. |
| 2003/0183015 A1 * | 10/2003 | Richardson et al. .......... 73/772 |
| 2004/0045365 A1 * | 3/2004 | Richardson .................. 73/772 |

FOREIGN PATENT DOCUMENTS

| | | |
|---|---|---|
| JP | 85018462 B | 5/1985 |
| JP | 2002060923 A | 2/2002 |

* cited by examiner

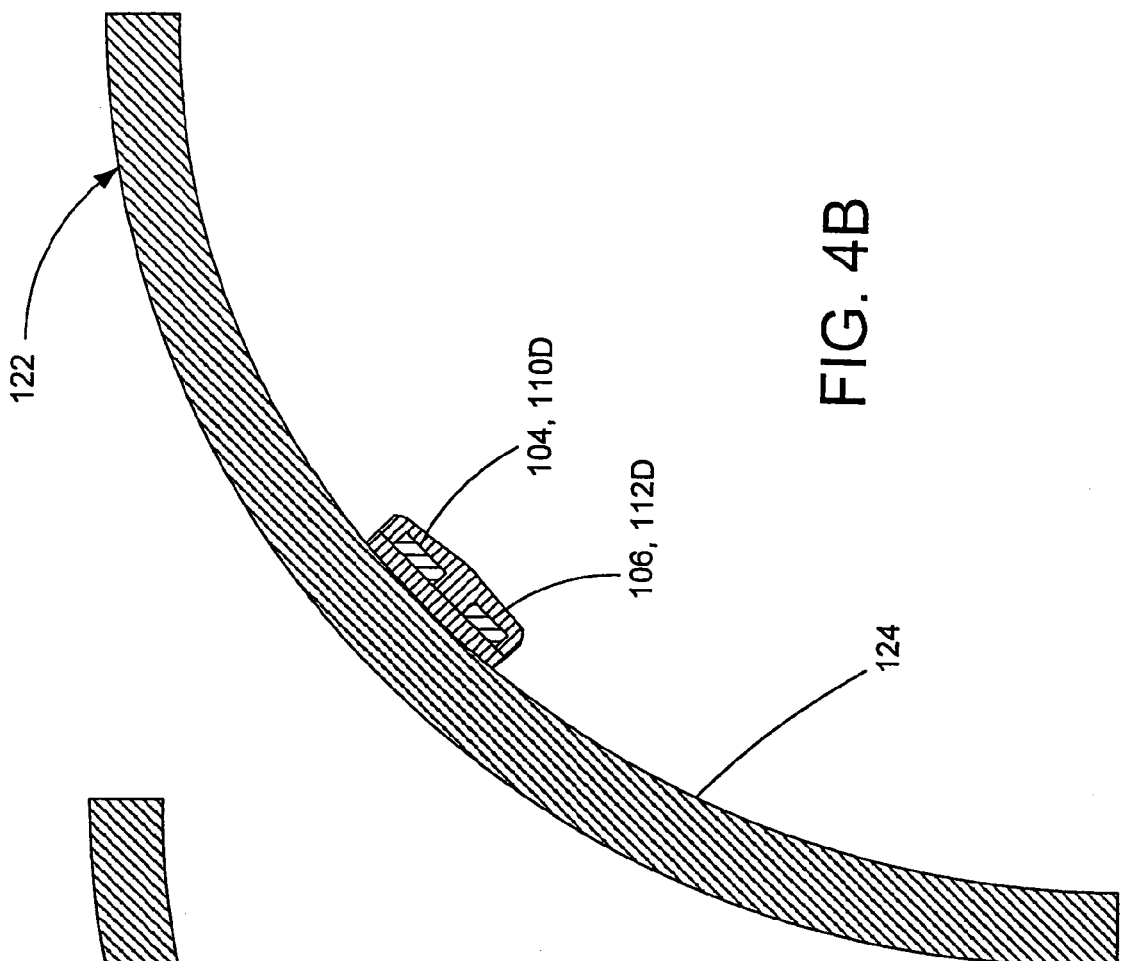
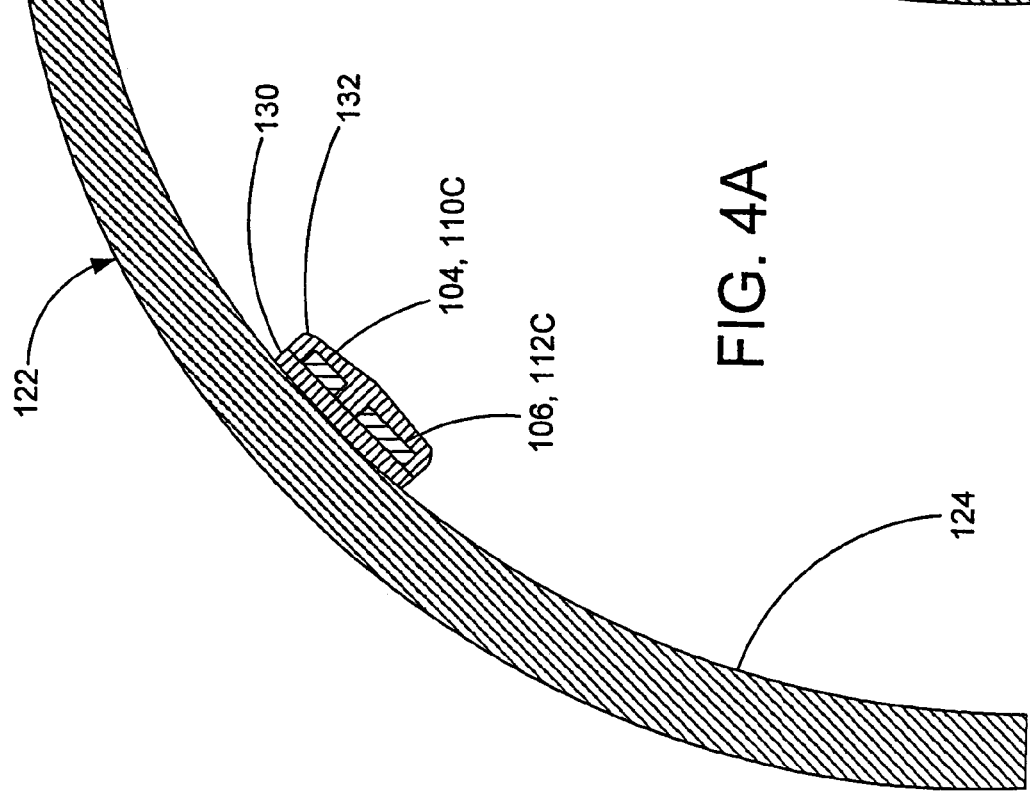

STRUCTURES INCLUDING NETWORK AND TOPOLOGY FOR IDENTIFYING, LOCATING AND QUANTIFYING PHYSICAL PHENOMENA

CROSS-REFERENCE TO RELATED APPLICATIONS

This application is a divisional of U.S. patent application Ser. No. 10/074,598 entitled NETWORK AND TOPOLOGY FOR IDENTIFYING, LOCATING AND QUANTIFYING PHYSICAL PHENOMENA, SYSTEMS AND METHODS FOR EMPLOYING SAME, filed on Feb. 11, 2002 now U.S. Pat. No. 6,884,557, which is also related to U.S. patent application Ser. No. 10/074,355 entitled SYSTEMS AND METHODS FOR COATING CONDUIT INTERIOR SURFACES UTILIZING A THERMAL SPRAY GUN WITH EXTENSION ARM, filed on Feb. 11, 2002.

GOVERNMENT RIGHTS

The United States Government has certain rights in this invention pursuant to Contract No. DE-AC07-99ID13727, and Contract No. DE-AC07-05ID14517between the United States Department of Energy and Battelle Energy Alliance, LLC.

BACKGROUND OF THE INVENTION

1. Field of the Invention

The present invention relates generally to a network and topology for detecting physical phenomena and for locating and quantifying the same. More particularly, the present invention relates to the use of a coded network implemented within a structure for detecting physical changes within the structure.

2. State of the Art

It is often desirable to detect and monitor physical changes within a structure. For example, it may be desirable to monitor pipes or other conduits for leaks or indications thereof so as to prevent collateral damage from such leaks. Similarly, it may be desirable to monitor the deformation of other structures, such as, for example, a bridge, a building, or even individual structural components of such facilities in order to determine actual or potential failures therein.

Various systems have been used to detect such physical changes. For example, one system used for detecting leaks in a pipe or other conduit is disclosed in U.S. Pat. No. 5,279,148 issued to Brandes on Jan. 18, 1994. The Brandes patent teaches a system which includes a first pipe for carrying a liquid medium and a second pipe which is coaxially located relative to the first pipe such that it encompasses the first pipe. A filler material is disposed in the annulus formed between the first and second pipes. Probes are inserted into the filler material at each end of the set of pipes to measure resistance of the filler material at each end of the pipe system relative to ground as well as between the two ends of the pipe system. Initial resistance measurements are used as a baseline value for future monitoring. Detection of significant deviation in the resistance measurements indicates a leak from the first pipe (i.e., the liquid medium has infiltrated the filler material thereby changing the resistivity/conductivity thereof). The change in resistance between the ends of the coaxial pipes as well as the change in resistance at each end of the coaxial pipes relative to ground may then be utilized to determine the location of the leak by comparing the ratio of the respective changes in resistance.

While such a system may be effective in detecting a leak within a pipe, it may also be cumbersome and expensive to implement, particularly since a second outer pipe is required to encapsulate the filler material about the liquid carrying pipe. Such a system would likely be difficult and cost prohibitive in retrofitting an existing layout of pipes or other conduits for leak detection. Also, the Brandes patent fails to disclose whether such a system would be effective for structures extending significant distances (i.e., several miles or longer) and with what resolution one may determine the location of a detected leak.

Further, such a system is only practical with respect to detecting a failure in a liquid carrying structure. If a transported liquid is not available to infiltrate the surrounding filler material and significantly change the electrical properties thereof, no detection will be made. Thus, such a system would not be applicable to detecting failure in various members of bridges, buildings or other such structures.

Another method of detecting fluid leaks includes the use of time domain reflectometry (TDR) such as is disclosed in U.S. Pat. No. 5,410,255 issued to Bailey on Apr. 25, 1995. TDR methods include sending a pulse down a transmission line and monitoring the reflection of such pulses. A change in the time of arrival or the shape of a reflected pulse indicates a leak based on, for example, a change in the structure of the transmission line and/or its interaction with the leaking medium. However, to implement a TDR system with, for example, a pipeline which extends for significant distances, special processing algorithms may have to be developed to enable rejection of spurious data for pipe joints or other discontinuities. Also, the types of transmission lines which may be used in such a TDR system may be restricted based on their electrical characteristics including the dielectric and resistivity characteristics of any insulation associated with such transmission lines.

Yet another approach detecting fluid leaks is disclosed in U.S. Pat. No. 4,926,165 to Lahlouh et al. on May 15, 1990. The Lahlouh patent teaches the use of two spaced apart conductors separated by a swellable member such that no electrical path exists between the two conductors in normal operating conditions. Upon occurrence of a leak, the swellable member swells to conductively contact the two conductors, creating an electrical short therebetween as an indication of a leak. However, such a device requires relatively complex construction including proper configuration of the conductors and swellable members. Additionally, the intrusion of a liquid other than that which may potentially leak from a pipe or conduit could trigger false indications of such leaks.

Additionally, as with the aforementioned Brandes patent, the method and device of the Lahlouh patent may only be used for detecting leaks in a liquid carrying structure and is not capable of detecting failures in other structures.

In view of the shortcomings in the art, it would be advantageous to provide a method and system for detecting, locating and quantifying physical phenomena such as leaks, strain and other physical changes within a structure. Further, it would be advantageous to provide monitoring of such physical phenomena to track potential failures of a structure for purposes of preventative maintenance.

It would further be advantageous to provide a method and system for detecting physical phenomena which is inexpensive, robust, and which may be implemented in numerous applications and with varying structures.

BRIEF SUMMARY OF THE INVENTION

In accordance with one aspect of the invention a method of monitoring a structure is provided. The method includes attaching a plurality of laterally adjacent conductors to the structure and defining each conductor of the plurality to include a plurality of segments coupled in series. Each of the segments are defined to have an associated unit value which is representative of a defined energy transmission characteristic. A plurality of identity groups is defined wherein each identity group includes a plurality of laterally adjacent segments and wherein each identity group includes at least one segment from each of the plurality of conductors. Energy is transmitted through the plurality of conductors and the plurality of conductors is monitored for a change in the defined energy transmission characteristic. A change in the defined energy transmission characteristic of one conductor may then be compared to the change in the defined energy transmission characteristic to at least one other conductor The method may further include determining from which identity group the change in the defined energy transmission characteristic originated. The determination of the originating identity group may include determining ratios of the change in the defined energy transmission characteristic from one conductor to another and comparing the ratios with a set of predetermined ratios which correspond to the ratios of unit values contained in individual identity groups.

In accordance with another aspect of the invention, a method is provided for detecting and monitoring a physical phenomena, such as, for example, strain induced within a structure. The method includes attaching a plurality of laterally adjacent conductors to the structure such that a physical phenomena exhibited by the structure in response to an applied physical condition will be substantially detected by the plurality of conductors. Each of the plurality of conductors is configured to exhibit a change resistance upon experiencing the physical phenomena. Each conductor is also defined to include a plurality of segments with each segment exhibiting an associated resistance value of the defined energy transmission characteristic. A plurality of identity groups is defined such that each identity group includes a plurality of laterally adjacent resistance segments and such that each identity group includes at least one resistance segment from each conductor. Energy is transmitted through each of the plurality of conductors and each of the conductors is monitored for a change in resistance. A detected change in resistance of a first conductor is then compared to a change in resistance of at least one other conductor.

In accordance with another aspect of the present invention, a system for detecting physical phenomena in a structure is provided. The system includes a plurality of laterally adjacent conductors with each conductor including a plurality of segments and wherein each segment is defined to have an associated unit value representative of a defined energy transmission characteristic. A plurality of identity groups is defined such that each identity group includes a plurality of laterally adjacent segments including at least one segment from each conductor. Each segment within an identity group is defined to exhibit an associated unit value such that the unit values in each identity group may be represented by a concatenated digit string of the unit values. Each identity group is defined so as to exhibit a unique concatenated digit string relative to the other identity groups.

In accordance with another aspect of the present invention, a structure is provided. The structure includes at least one structural member having a plurality of conductors attached thereto. Each conductor of the plurality includes a plurality of segments. A plurality of identity groups is defined such that each identity group includes a plurality of segments including at least one segment from each conductor. Each segment within an identity group is defined to exhibit an associated unit value representative of an energy transmission characteristic such that the unit values of each identity group may be represented by a concatenated digit string of the unit values contained therein. The unit values are further defined such that each concatenated digit string is unique.

BRIEF DESCRIPTION OF THE SEVERAL VIEWS OF THE DRAWINGS

The foregoing and other advantages of the invention will become apparent upon reading the following detailed description and upon reference to the drawings in which:

FIGS. 4A and 4B are partial section views taken along the lines indicated in FIG. 3;

DETAILED DESCRIPTION OF THE INVENTION

Figure 1:
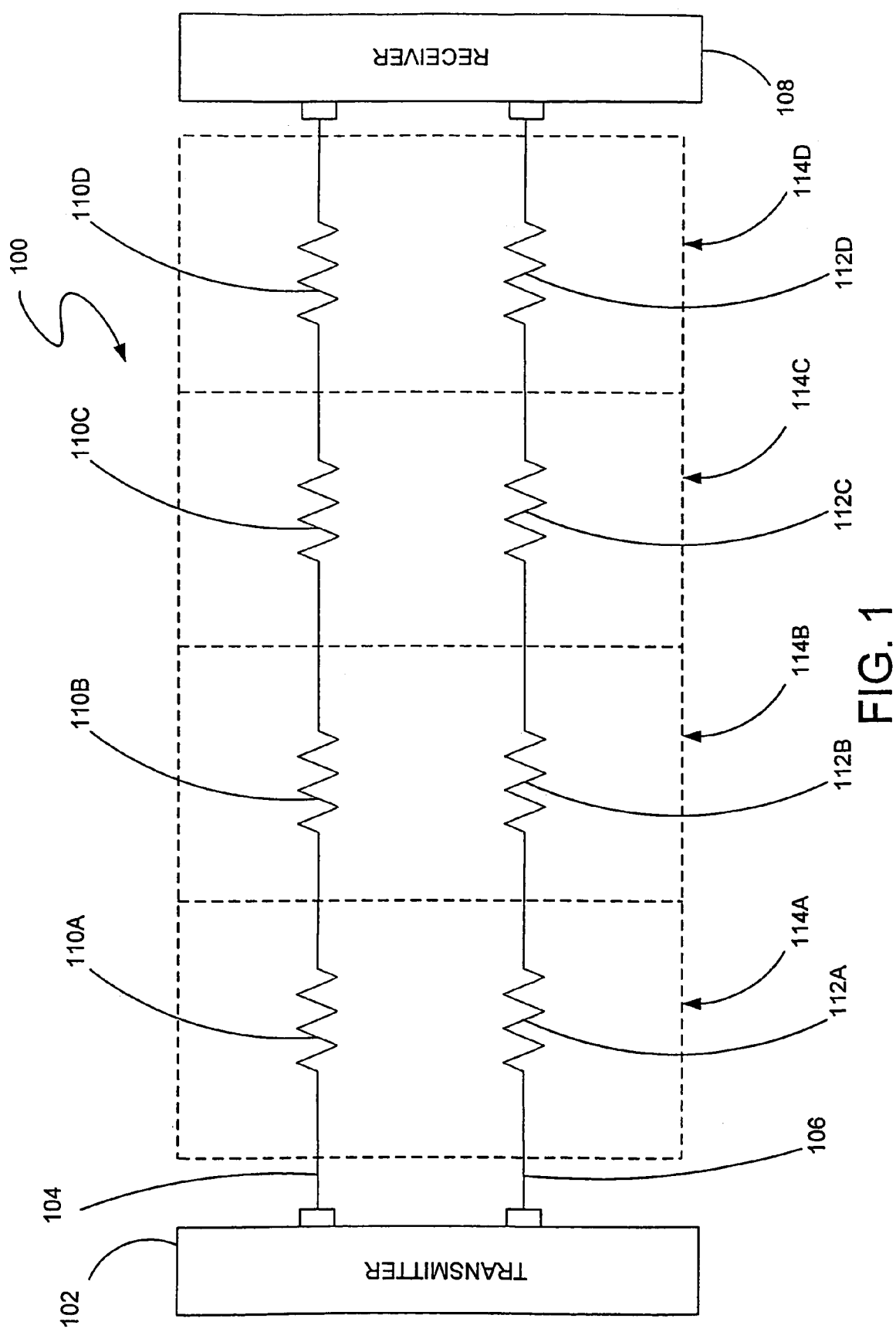
FIG. 1 is a schematic of a network and topology used in detecting a physical phenomena according to one embodiment of the present invention.

Referring to FIG. 1, a network 100 is shown for detecting a physical phenomena according to an exemplary embodiment of the present invention. The network 100 includes a transmitter 102 operatively coupled with a first conductor 104 and a second conductor 106 at first adjacent ends thereof. The two conductors 104 and 106 are each coupled at an opposing end to a receiver 108. The conductors 104 and 106 may be any of a number of different energy transmitting mediums, including, for example, conductive traces, semiconductive traces or optical fibers and, thus, the term "conductors" is used herein to encompass any such energy transmitting medium. Similarly, while the terms "transmitter" and "receiver" are used herein, such are used in the generic sense of being able to transmit energy (including, for example, electrical energy or light energy) and receiving and detecting the transmitted energy.

The first and second conductors 104 and 106 are positioned laterally adjacent one another and are defined to include a plurality of segments 110A–110D and 112A–112D respectively which, for sake of convenience, shall be referred to herein with respect to the exemplary embodiments as resistance segments. As with the various terms discussed above, the term "resistance segment" is used generically to indicate a defined level of resistance to the energy flow which is being transmitted through the conductors 104 and 106.

Furthermore, while the exemplary embodiments discuss the use of "resistance segments," the present invention may be practiced with a plurality of segments wherein each segment is defined to exhibit a unit value which is representative of a specified energy transmission characteristic other than resistance to energy flow. Additionally, discussion below with regard to the exemplary embodiments of detecting or measuring "changes in resistance" is equally applicable to detecting and measuring a change in the specified energy transmission characteristic.

Referring still to FIG. 1, the resistance segments 110A–110D of the first conductor 104 are operatively connected in series with one another. Likewise, the resistance segments of the second conductor 106 are operatively connected in series with one another. It is noted that, while the exemplary embodiment of the network 100 is shown using two conductors 104 and 106 with each having four resistance segments 110A–110D and 112A and 112D respectively, the invention may be practiced with other combinations of conductors and resistance segments as shall be discussed in greater detail below.

A plurality of identity groups 114A–114D are formed of laterally adjacent resistance segments 110A–110D and 112A–112D respectively. Thus, identity group 114A comprises resistance segments 110A and 112A, identity group 114B comprises resistance segments 110B and 112B and so on.

Figure 2:
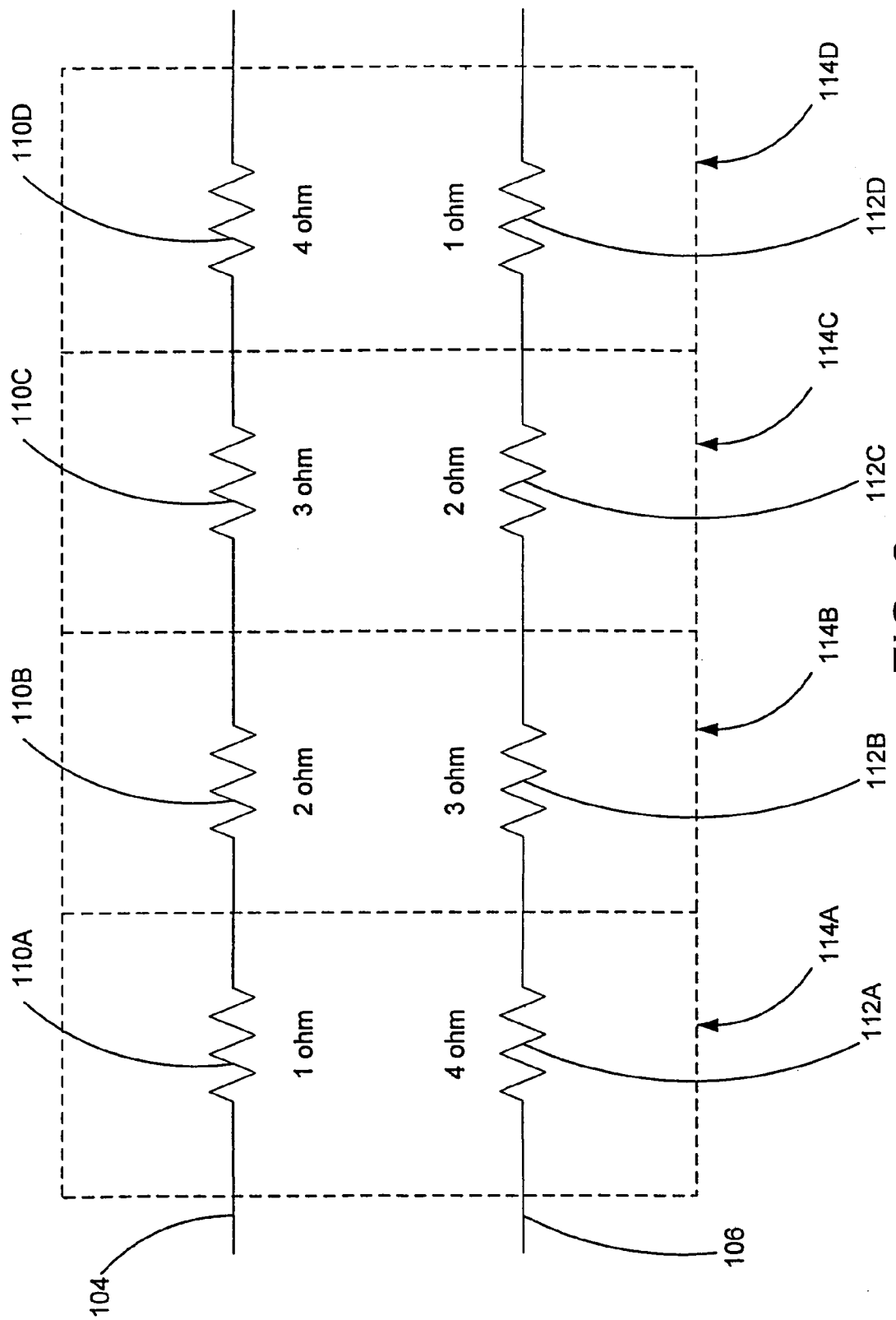
FIG. 2 is a schematic view of a portion of the network shown in FIG. 1.

Referring to FIG. 2, and using an example of conductors 104 and 106 comprising conductive traces or other electrically conductive members, the resistance segments 110A–110D and 112A–112D are assigned exemplary unit resistance values, in this case expressed in the unit ohms for electrical resistance. The assigned, or defined unit resistance values are as shown in FIG. 2 with resistance segment 110A having a unit resistance value of 1 ohm, resistance segment 112A has a unit resistance segment of 4 ohms, and so on. Further, each identity group may be identified by a concatenated digit string which is representative of the actual or normalized unit resistance values contained therein. Thus, identity group 114A may be represented by the digit string "14" based on the unit resistance values for resistance segments 110A and 112A. Similarly, identity group 114B may be represented by the digit string "23", identity group 114C by the digit string "32" and identity group 114D by the digit string "41."

It is noted that the concatenated digit string for each identity group 114A–114D is a unique number in comparison with the concatenated digit strings for every other identity group within the network 100. Further, it is noted that the ratios of the unit resistance values within a group identity are likewise unique. For example, the ratio of unit resistance values in identity group 114A is 1:4 or 0.25. In comparison, the ratio for identity group 114B is 2:3 or 0.667, for identity group 114C is 3:2 or 1.5 and for identity group 114D is 4:1 or simply 4. The identity of such ratios, as well as the uniqueness each of the various ratios, assist in detecting, locating and quantifying a physical phenomena as shall become more apparent below.

Figure 3:
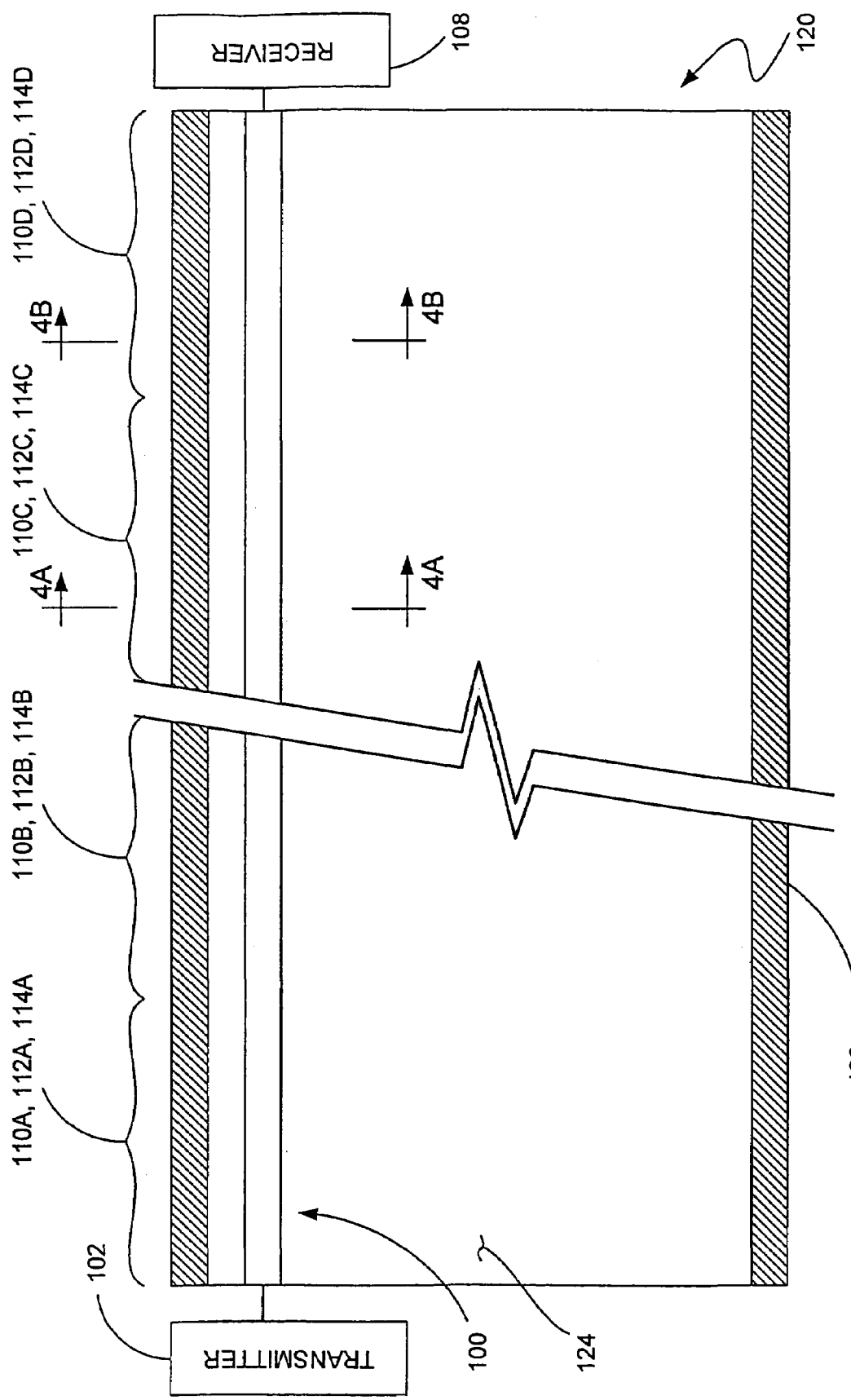
FIG. 3 is a partial cross-sectional view of a structure incorporating a network according to an embodiment of the present invention.

Referring to FIG. 3, a network such as described above is incorporated into a structure 120 which, in the exemplary embodiment, is shown as a conduit 122 such as, for example, a part of a pipeline for carrying a fluid medium. The network 100 is formed on the interior surface 124 of the conduit 122, although other locations, including the exterior of the pipeline, are also suitable. Generally, the network 100 may be formed on the surface of, or embedded within, any of a number of different structures, which may be referred to more generically as a substrate.

In the case of a pipeline or conduit 122, it may be desirable to detect strain or deformation within the structure 120 so as to determine potential failures which, in this case, may result in leakage of fluid from the conduit. Thus, for example, if the conduit 122 exhibits deformation or strain in an area associated with identity group 114B, resistance segments 110B and 112B, which are coupled with the surface 124 of the conduit 122, will likewise exhibit the strain or deformation. If the conductors 104 and 106 are electrical type-conductors, the resistance segments 110B and 112B will exhibit a change in resistivity upon experiencing an induced strain. Thus, a change in resistance measured across the conductors 104 and 106 indicates a deformation in the structure. It is noted that if the conductors are positioned closely enough, a substantial deformation in the structure 120 to which they are attached should induce strain in both conductors 104 and 106. Thus, certain anomalies wherein a resistance change in one conductor 104 but not another 106 may be substantially accounted for.

It is also noted that if the conductors 104 and 106 are of a different type of energy transmitting medium, such as, for example, optical fibers, some other property will exhibit a change, such as a phase change of the light signal traveling through optic fibers, upon experiencing a strain therein.

Furthermore, while the exemplary embodiments set forth herein are described in terms of detecting strain or transformation, other physical phenomena may be detected, located and quantified. For example, the physical phenomena may include changes due to temperature, corrosion, wear due to abrasion, chemical reactions or radiation damage as experienced by the conductors.

Still using electrical conductors 104 and 106 as an example, the change in resistivity in each resistance segment 110B and 112B will be a function of the unit resistance values respectively associated therewith. By determining the ratio of the change in resistance measured by a receiver 108 through each of the conductors 104 and 106, the location of the strain may be determined.

For example, referring back to FIG. 2, a strain induced in the resistance segments 110B and 112B of identity group 114B will result in a change of resistivity in each conductor 104 and 106. It is noted that upon initial implementation of the network 100 the overall resistance of a conductor 104 and 106 may be measured and utilized as a baseline value. Any subsequent measurements of resistance may then be compared to the baseline value to detect whether a change in resistance has occurred or not. The conductors 104 and 106 may be checked for resistance changes at a predetermined sample rate, such as, for example, once per second. Of course other sample rates may be utilized according to specific applications and monitoring requirements.

It may be the case that once a change in resistance has been detected that the measured value of resistance may not return to its original baseline value. For example, a change in resistance may be due to a permanent deformation in an associated structure. Thus, it may be required to set a new baseline value (or re-zero the values) of the overall measured resistance in the conductors 104 and 106 after the detection of a change in resistance.

The measured change in resistance detected in the conductors 104 and 106 is a function of the unit resistance values of the individual resistance segments 110B and 112B (e.g., it is a function of, in this example proportional to, the values of 2 ohms and 3 ohms respectively). Thus, by taking the ratio of the change in resistance measured by the receiver (i.e., $\Delta R_{104}/\Delta R_{106}$, where $\Delta R$ is the change in resistance for the specified conductor), the ratio may be compared to the ratios of the unit resistance values of each identity group 114A–114D to determine the location of the strain. In this case, strain exhibited in the region encompassed by identity group 114B will exhibit itself as a change in resistance in both conductors 104 and 106, the ratio of which change will be a function of the ratio 2:3 or 0.667 which is equal to the ratio of the unit resistance values thereof. The detection of strain or deformation within identity groups 114A, 114C or 114D would likewise yield, with regard to the change in resistance in the conductors 104 and 106, functions of the ratios 0.25, 1.5 and 4 respectively.

Having located the area of deformation (e.g., within identity group 114B) the magnitude of the strain may then be calculated. As will be appreciated by one of ordinary skill in the art, the change in resistance measured by the receiver 108 for a particular conductor 104 or 106 is a function of the unit value resistance associated with the resistance segment (e.g. 110B or 112B) in which the strain was detected. Thus, by knowing the unit value of resistance for a particular resistance segment in which strain has been detected, the amount of change in resistance exhibited by a conductor and the relationship between strain and resistance for a conductor of a given configuration and material composition, one can calculate the amount of strain exhibited by the conductors 104 and 106 and thus the amount of strain induced in any associated structure 120 to which they are attached.

For example, having located a strain in identity group 114B, and assuming the use of electrical traces for conductors 104 and 106 and assuming linear proportionality between change in resistance and unit resistance, one could determine the magnitude of the strain using the following equations:

$$\text{DEFORMATION} = \frac{\delta\varepsilon(R)}{\delta(R)} \frac{\Delta R_{104}}{2}$$

for the strain exhibited in conductor 104, and;

$$\text{DEFORMATION} = \frac{\delta\varepsilon(R)}{\delta(R)} \frac{\Delta R_{106}}{3}$$

for the strain exhibited in conductor 106 where $\varepsilon(R)$ is represents the relationship between resistance and strain for a given resistance segment, $\Delta R$ represents magnitude of the change of resistance measured in a given conductor and wherein the numeral denominator represents the unit resistance value for the particular resistance segment in which strain was detected (i.e., the "2" in the first equation is for resistance segment 110B, and the "3" in the second equation is for resistance segment 112B).

As has been noted above, one embodiment may include the use of conductive traces for conductors 104 and 106. Referring to FIGS. 4A and 4B, a partial cross-sectional view is shown of conductors 104 and 106 utilizing conductive traces according to one embodiment. As is indicated in FIG. 3, FIG. 4A is a view depicting the resistance segments in identity group 114C while FIG. 4B is a view depicting the resistance segments in identity group 114D.

The conductors 104 and 106, shown as conductive traces, may be attached to a structure 102, such as the conduit 122, by a thermal spray process. In order to apply the conductive traces to a structure 120, including one in which the surface may be degraded and/or conductive, it may be desirable to provide an insulative layer 132 directly on the surface 124 of the structure (e.g., the conduit 122). The insulative layer 132 keeps the conductors 104 and 106 from forming an electrical connection with the structure 120, and also provides a uniform surface on which to form the conductors 104 and 106. One insulative layer 130 may be formed and sized such that all of the conductors 104 and 106 may be formed thereon or, alternatively, an individual layer 130 may be formed for each individual conductor 104 and 106 as may be desired. A second insulative layer 132 may be formed to encompass or encapsulate the conductors 104 and 106 from each other and from the surrounding environment. It is noted, however, that if physical phenomena such as corrosion or abrasion is being detected, located and/or quantified, that the second insulative layer 132 would not be needed.

Such an embodiment as shown in FIGS. 4A and 4B may include, for example, an insulative layer 130 formed of alumina, conductive traces of nickel-aluminum, and a second insulative layer 132 of alumina. Other materials may also be suitable such as, for example, copper or other conductive materials for the conductors 104 and 106. Likewise other materials may be utilized in forming the insulative layers 130 and 132.

An embodiment such as that shown in FIGS. 4A and 4B may be formed by thermal spraying of the insulative layers 130 and 132 and/or the conductive traces (which form the conductors 104 and 106). In one exemplary embodiment, a thermally sprayed insulative layer 130 may be approximately 0.5 inches wide and 0.12 to 0.15 inches thick. A conductive trace acting as a conductor 104 or 106 may be formed with a width of approximately 0.3 inches and a thickness of approximately 0.007 inches. One such exemplary conductive trace was formed on the interior of an eight inch long piece of square tubing and exhibited an electrical resistance of 4.1 ohms under no-load conditions. The same conductive trace exhibited a change in resistance to approximately 38 ohms when the tubing was subjected to three-point bending with a loading of approximately 40,000 pounds. The conductive trace returned to 4.1 ohms upon removal of the three-point bending load.

An exemplary thermal spraying device which may be used in conjunction with the application such insulative layers 130 and 132 and/or conductors 104 and 106 is disclosed in pending U.S. patent application Ser. No. 10/074,355 entitled SYSTEMS AND METHODS FOR COATING CONDUIT INTERIOR SURFACES UTILIZING A THERMAL SPRAY GUN WITH EXTENSION ARM, filed on even date herewith and which is assigned to the assignee of the present invention, the entirety of which is incorporated by reference herein.

Figure 5:
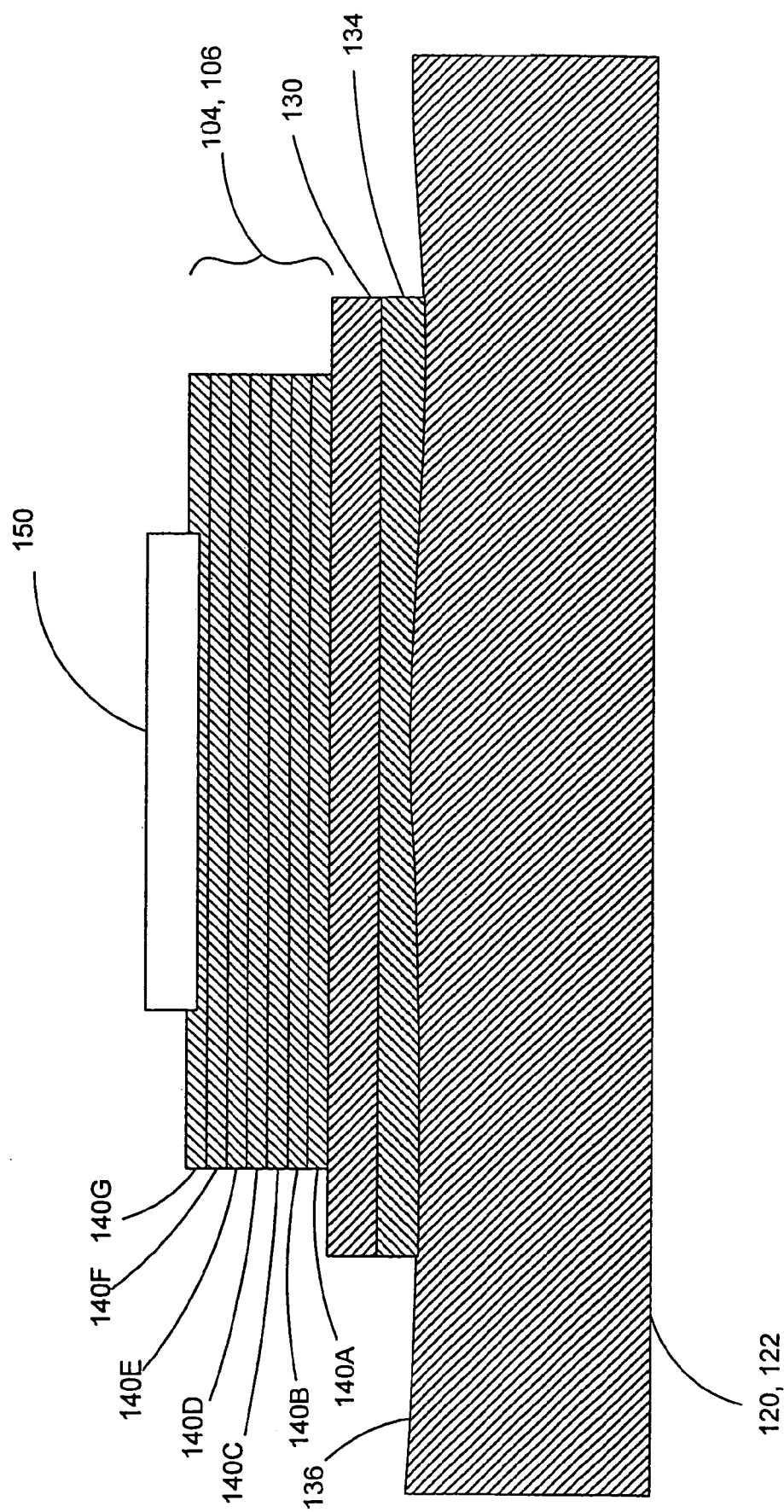
FIG. 5 is a partial cross-sectional view of a structure and an associated network for detecting physical phenomena according to an aspect of the present invention.

Referring briefly to FIG. 5, the conductors 104 and 106, when in the form of electrical conductive traces, may be formed by building up individual layers 140A–140G until a desired thickness or height of the conductors 104 and 106 is obtained. Likewise, if so desired or needed, the insulative layers 130 and 132 may be layered to obtain a desired thickness or height. Further, if so needed, a bonding agent or bonding layer 134 may be used between the insulative layer and a surface 136 of the structure 120 if the surface exhibits a degree of degradation.

As can be seen by comparing the conductors 104 and 106 from FIG. 4A to FIG. 4B the conductors 104 and 106 may vary in cross sectional area from one resistance segment to another (i.e., from 110C to 110D and from 112C to 112D). The change in cross-sectional area of the conductors 104 and 106 may be effected by varying their width (such as shown), their height or some combination thereof. Of course other cross-sectional areas are contemplated and the variance thereof may depend on other variables, such as for example, a diameter of the cross-sectional area.

Changing the cross-sectional area of the conductors 104 and 106 is one way of defining unit resistance values for the plurality of resistance segments 110A–110D and 112A–112D. Alternatively, the unit resistance values may be defined by utilizing different materials or varying the material compositions for the individual resistance segments 110A–110D and 112A–112D. For example, a first resistance segment 110A may be formed of a first material exhibiting a first resistivity while the next adjacent resistance segment 110B may be formed of another material which exhibits a different resistivity. Alternatively, some property of the material, such as, for example, porosity, may be altered from one resistance segment 110A to the next 110B. For example, in thermally sprayed conductive traces, the unit resistance may also be a function of the size of the droplets being sprayed to form the trace, as well as other properties associated with the bonding surfaces of such droplets.

Referring back now to FIGS. 1 and 2, as noted above, the network 100 shown is exemplary, and numerous variations may be made in order to implement the network 100 in specific systems or structures. For example, if such a network installed into a structure such as pipeline, or a section thereof, more conductors than just two may be desired so as to refine the resolution of the network 100 for locating a strain or other physical phenomena detected thereby.

Such a pipeline may include multiple lengths of twenty miles or longer between which lengths structures known as "pig traps" (for insertion and removal of "pigs" as is known in the art) may be formed. Thus, it may be desirable to extend a plurality of conductors for a length as great as twenty miles or more. Thus, using a twenty mile section of a pipeline as an example, it will become desirable to locate the situs of the detected physical phenomena within a given range of distance along that twenty mile section. Such a network 100 becomes much more valuable when the resolution with regard to locating the situs of the physical phenomena is refined to within a physically searchable distance such as, for example, tens of feet.

In determining how many conductors should be used for such an application, the number of resistance segments formed in a given conductor and how many different unit resistance values may be assigned to the plurality of conductors must be known. It is noted that the number of different unit resistance values which may be used will determine the number base (i.e., base 10, base 8, etc.) will be used in numerically representing the unit resistance values of each resistance segment.

With respect to the number of resistance segments, considering a distance of twenty miles and assuming a resolution of approximately plus or minus twenty feet, one may determine that there will be 5,280 segments in a given conductor (i.e., (20 miles×5,280 feet/mile)/20 feet/segment=5,280 segments).

To determine the number of different unit resistance values which may be used in a given conductor, the uncertainty with respect to the construction of the resistance segments must be considered. For example, considering electrical traces being used as conductors, the uncertainty associated with the cross-sectional area of the trace must be considered. The uncertainty in cross-sectional area of a conductive trace may include combined uncertainties of both width and thickness (or height). Additionally, uncertainty may be affected by the mode of construction of the conductive traces. For example, building up a conductive trace by thermally spraying multiple layers (such as in FIG. 5) has an affect on the overall certainty of the resultant height as will be appreciated by those of ordinary skill in the art. Such values of uncertainty may be determined through statistical analysis, experimentation or a combination thereof as will also be appreciated by those of ordinary skill in the art.

For sake of example, considering the uncertainty in the cross-sectional area of a conductive trace to be less than 10%, say for example 9.9%, one may determine that the maximum number of useful unit resistance values which may be assigned to the individual resistance segments of a conductor is ten (i.e., Max.#$\leq$100/9.9$\leq$10.1). Thus, the base number for the above example would be base ten, or in other words, ten different unit resistance values may be assigned to resistance segments of a conductor.

Knowing that 5,280 resistance segments will be used, and that ten different unit resistance values will be used, one may determine the number of conductors which will be needed to provide 5,280 unique concatenated digit strings for the identity groups. It is desirable that the unique concatenated digit strings each represent a prime number since the use of a prime number guarantees the ratios of all the unit resistance values represented thereby will be unique. For example, considering a four digit prime number of "ABCD", each ratio of A:B, A:C, A:D, B:C, B:D and C:D will be unique. It is noted that no concatenated digit string should include a zero digit, as an electrical trace may not be constructed to include a resistance segment having a unit resistance value of zero.

The number of prime numbers available for a particular digit string may be determined using one or more of various algorithms or databases known and available to those of ordinary skill in the art. For example, the University of Tennessee at Martin has published various lists of prime numbers including a list of the first 100,008 prime numbers (also referred in the publication as "small primes"). Such a list allows for the determination of the number of nonzero primes up to six digits in base ten. Using such a database or publication it may be determined that the number of five digit nonzero primes is 6,125. Thus, five conductors may be used to formed a network of 5,280 resistance segments per conductor (and thus 5,280 identity groups with associated concatenated digit strings) with each resistance segment being twenty feet long.

The operation of the five-conductor network would then be similar to that described above with respect to FIGS. 1 through 3 wherein resistance changes would be detected with associate ratios of such resistance changes being compared to a database of ratios associated with the 5,280 identity groups to locate a situs of strain or some other physical phenomena. Of course, it is noted that, while the use of a five-conductor network may be adequate for coding an resolution issues presented above, it may be desirable to provide one or more conductors (e.g., a six- or seven-conductor network) for fault tolerance purposes. Thus, with fault tolerance, even if a conductor within the network fails, adequate coding will remain in place to sufficiently identify, locate and quantify a physical phenomena.

It is also noted that the resolution may be improved over a given length by either improving the uncertainty associated with the construction of the conductors, or by including a greater number of conductors. For example, the number of conductors in the above scenario may be increased to obtain a resolution of plus or minus ten feet, five feet or less if so desired.

Referring back to FIG. 5, it is noted that either in conjunction with a network 100 (FIG. 1), or independent therefrom, conductors 104 and 106 may be attached to a structure 120 for use in carrying other signals and measuring other values associated with the structure 120. For example, one or more sensors 150 or other microinstrumentation may be attached to, or embedded in, a conductor 104 and 106 for purposes of measuring or detecting pressure, temperature, flowrate, acoustic signals, chemical composition, corrosion or data transmission anomalies. Conductors 104 and 106, such as the conductive traces described above herein, have the ability to extend for substantial distances (e.g. several miles) without substantial degradation in signal transmission. Thus, one or more of such conductors may also be utilized as a communications link if so desired.

Figure 6:
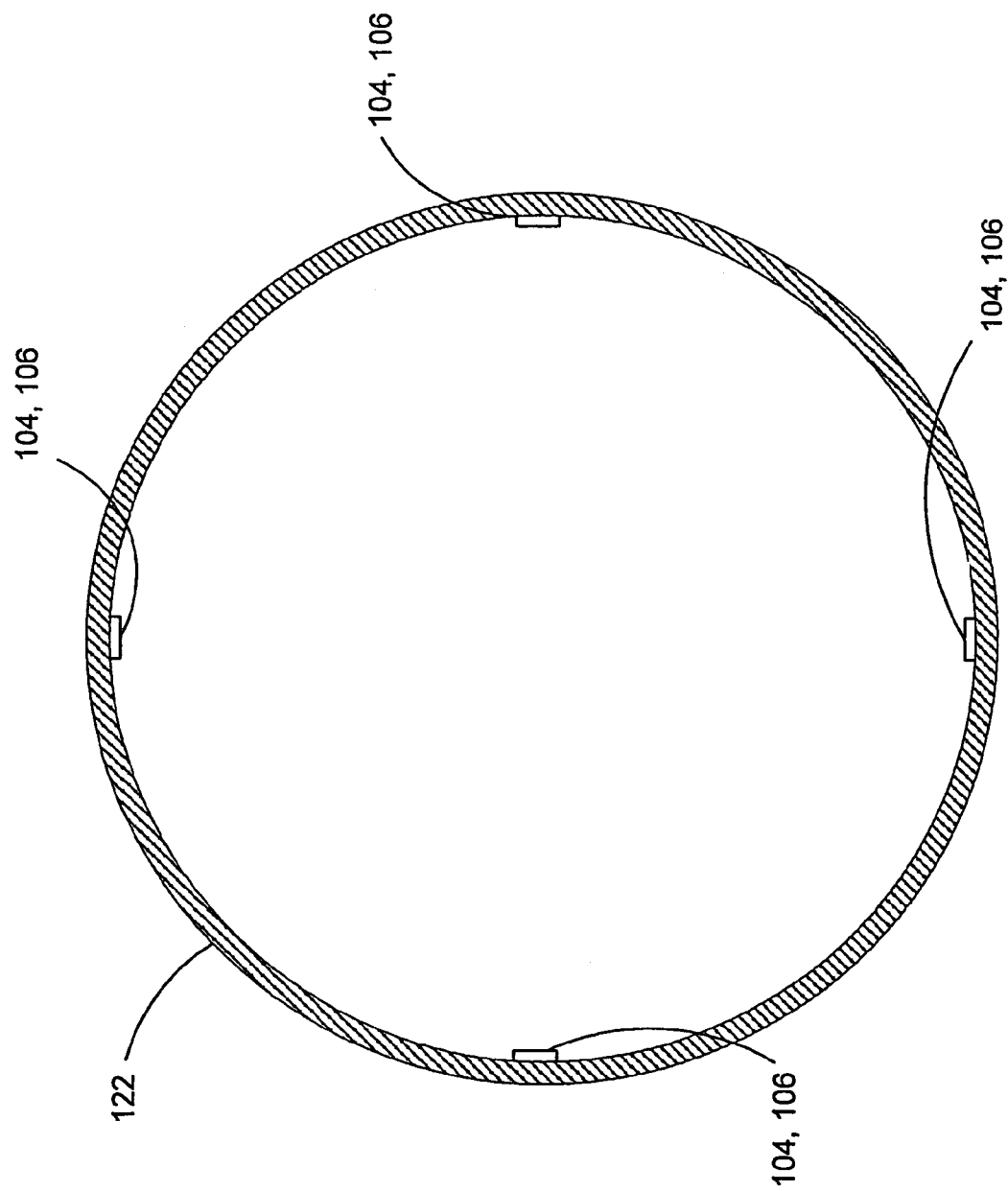
FIG. 6 is a cross-sectional view of a conduit with associated conductors in accordance with an embodiment of the present invention.

As shown in FIG. 6, such traces or other conductors 104 and 106 may be installed in a conduit 122 or other structure in a predetermined geometric arrangement so as to detect strain or some other physical phenomena at various locations within the structure. For example, FIG. 6 shows a plurality of conductors 104 and 106 angularly displaced about a circumference of the conduit 122 and configured to coextensively and longitudinally extend with the length of the conduit 122. Such an arrangement allows for detection of a strain or other physical phenomenon which occurs on only a portion of the structure.

Thus, a plurality of networks may be disposed on a single structure. Alternatively, individual conductors might be spaced about the circumference with each carrying one or more sensors therewith. Of course other geometrical configurations may be utilized. For example, one or more networks (or alternatively, individual conductors) may be configured to extend from one end of a conduit 122 to another in a helical pattern about a circumference thereof.

It is noted that the exemplary embodiments set forth above may be incorporated into any number of structures including stationary structures well as mobile structures. For example, such a system could be employed in bridges, dams, levees, containment vessels, buildings (including foundations and other subsurface structures), aircraft, spacecraft, ground transport vehicles or various components thereof. Indeed, the system may be utilized with virtually any structure wherein detection, location and quantification of a specified physical phenomena is required.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention includes all modifications, equivalents, and alternatives falling within the spirit and scope of the invention as defined by the following appended claims.

We claim:

1. A structure comprising:
    at least one structural member;
    a plurality of conductors attached to the at least one structural member, each conductor of the plurality including a plurality of segments coupled in series;
    a plurality of identity groups, each identity group including a plurality of laterally adjacent segments including at least one segment from each conductor, wherein each segment within an identity group exhibits an associated unit value representative of a defined energy transmission characteristic such that the unit values of each identity group may be represented by a concatenated digit string of the unit values contained therein and wherein the concatenated digit string of each identity group of the plurality is unique.

2. The structure of claim 1, wherein the at least one structural member comprises at least one conduit for conveying a fluid medium and wherein the plurality of conductors are attached to an interior surface of the at least one conduit.

3. The structure of claim 2, wherein the plurality of conductors includes conductive traces and wherein each conductive trace is insulated from each other conductive trace.

4. The structure of claim 2, wherein each of the plurality of conductors comprises a length of approximately twenty miles.

5. The structure of claim 2, wherein the each of the plurality of segments comprises a length of approximately twenty feet.

6. The structure of claim 1, wherein each of the plurality of conductors includes a thermally sprayed conductive trace comprising a nickel aluminum alloy.

7. The structure of claim 3, further comprising a layer of thermally sprayed alumina disposed between each conductive trace and a surface of the at least one structural member.

8. The structure of claim 1, wherein each concatenated digit string is representative of a prime number.

9. The structure of claim 1, wherein each segment is configured to exhibit a change in the defined energy transmission characteristic upon experiencing a strain therein.

10. The structure of claim 1, wherein a plurality of ratios are defined between the associated values of each segment of a given identity group and each other segment of the given identity group and wherein each of the plurality of ratios within the given group are unique.

11. The structure of claim 1, wherein the associated unit value of each of the plurality of segments corresponds to a cross-sectional area exhibited by the associated segment as taken substantially transverse to a length thereof.

12. The structure of claim 1, wherein the associated unit value of each of the plurality of segments corresponds to a material porosity thereof.

13. The structure of claim 1, wherein the associated unit value of each of the plurality of segments corresponds to a material composition thereof.

14. The structure of claim 1, wherein the plurality of conductors includes at least five conductors.

15. The structure of claim 1, wherein the plurality of conductors comprises optical fibers.

16. The structure of claim 1, further comprising a transmitter coupled to a first end of each of the plurality of conductors and configured to transmit energy through the plurality of conductors.

17. The structure of claim 16, further comprising a receiver coupled to a second end of each of the plurality of conductors and configured to detect an energy transmission from each of the plurality of conductors.

18. The structure of claim 1, further comprising at least one sensor attached to the structural member.

19. The structure of claim 18, wherein the at least one sensor is operatively coupled to at least one of the plurality of conductors.

20. The structure of claim 18, further comprising at least one other conductor attached to the at least one structure member and wherein the at least one sensor is operatively coupled to at least one other conductor.

* * * * *